United States Patent
Zoromski et al.

(10) Patent No.: US 7,723,422 B2
(45) Date of Patent: May 25, 2010

(54) FUNCTIONALIZED BLOCK COPOLYMERS

(75) Inventors: Michele L. Zoromski, Minneapolis, MN (US); Liliana L. Atanasoska, Edina, MN (US); Robert W. Warner, Woodbury, MN (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 1187 days.

(21) Appl. No.: 11/317,614

(22) Filed: Dec. 23, 2005

(65) Prior Publication Data

US 2007/0149690 A1     Jun. 28, 2007

(51) Int. Cl.
C08K 3/40 (2006.01)
(52) U.S. Cl. .................................. 524/494; 524/543
(58) Field of Classification Search ................ 524/494, 524/543
See application file for complete search history.

(56) References Cited

U.S. PATENT DOCUMENTS

| | | | |
|---|---|---|---|
| 4,003,874 A | 1/1977 | Ide et al. | |
| 4,868,967 A | 9/1989 | Holt et al. | |
| 5,070,597 A | 12/1991 | Holt et al. | |
| 5,218,033 A * | 6/1993 | Pottick et al. ............. | 524/399 |
| 5,674,698 A | 10/1997 | Zarling et al. | |
| 5,698,397 A | 12/1997 | Zarling et al. | |
| 5,736,410 A | 4/1998 | Zarling et al. | |
| 5,807,944 A | 9/1998 | Hirt et al. | |
| 5,824,717 A | 10/1998 | Merrill et al. | |
| 5,876,432 A | 3/1999 | Lau et al. | |
| 5,891,656 A | 4/1999 | Zarling et al. | |
| 6,001,123 A | 12/1999 | Lau | |
| 6,017,362 A | 1/2000 | Lau | |
| 6,053,214 A | 4/2000 | Sjoberg et al. | |
| 6,159,686 A | 12/2000 | Kardos et al. | |
| 6,165,210 A | 12/2000 | Lau et al. | |
| 6,312,914 B1 | 11/2001 | Kardos et al. | |
| 6,399,397 B1 | 6/2002 | Zarling et al. | |
| 6,422,575 B1 | 7/2002 | Czaplicki et al. | |
| 6,537,829 B1 | 3/2003 | Zarling et al. | |
| 6,613,066 B1 | 9/2003 | Fukaya et al. | |
| 6,630,221 B1 | 10/2003 | Wong | |
| 6,846,892 B2 | 1/2005 | Kindt-Larsen et al. | |
| 6,855,743 B1 | 2/2005 | Gvozdic | |
| 6,884,628 B2 | 4/2005 | Hubbell et al. | |
| 6,949,112 B1 | 9/2005 | Sridharan et al. | |
| 2002/0045706 A1 | 4/2002 | Houston et al. | |
| 2002/0096833 A1 | 7/2002 | Czaplicki et al. | |
| 2002/0128234 A1 | 9/2002 | Hubbell et al. | |
| 2002/0165523 A1 | 11/2002 | Chin et al. | |
| 2002/0193030 A1 | 12/2002 | Yao et al. | |
| 2003/0004564 A1 | 1/2003 | Elkins et al. | |
| 2003/0020870 A1 | 1/2003 | Soane et al. | |
| 2003/0040771 A1 | 2/2003 | Hyodoh et al. | |
| 2003/0040772 A1 | 2/2003 | Hyodoh et al. | |
| 2003/0149475 A1 | 8/2003 | Hyodoh et al. | |
| 2003/0163148 A1 | 8/2003 | Wang et al. | |
| 2003/0201572 A1 | 10/2003 | Coon et al. | |
| 2003/0209921 A1 | 11/2003 | Coon et al. | |
| 2003/0211799 A1 | 11/2003 | Yao et al. | |
| 2003/0236376 A1 | 12/2003 | Kindt-Larsen et al. | |
| 2004/0044397 A1 | 3/2004 | Stinson | |
| 2004/0093008 A1 | 5/2004 | Zamore | |
| 2004/0132923 A1 | 7/2004 | Shalaby | |
| 2004/0133062 A1 | 7/2004 | Pai et al. | |
| 2004/0144655 A1 | 7/2004 | Bertrand et al. | |
| 2004/0171740 A1 | 9/2004 | Ruberti et al. | |
| 2004/0230309 A1 | 11/2004 | DiMauro et al. | |
| 2004/0256842 A1 | 12/2004 | Breed | |
| 2004/0266941 A1 | 12/2004 | Houston et al. | |
| 2005/0004663 A1 | 1/2005 | Llanos et al. | |
| 2005/0015046 A1 | 1/2005 | Weber et al. | |
| 2005/0031852 A1 | 2/2005 | Schmidt et al. | |
| 2005/0031872 A1 | 2/2005 | Schmidt et al. | |
| 2005/0033256 A1 | 2/2005 | Schmidt et al. | |
| 2005/0042298 A1 | 2/2005 | Pardridge et al. | |
| 2005/0043474 A1 | 2/2005 | Schmidt et al. | |
| 2005/0049323 A1 | 3/2005 | Gvozdic | |
| 2005/0049691 A1 | 3/2005 | Mericle et al. | |

(Continued)

FOREIGN PATENT DOCUMENTS

EP     0 380 236     5/1995

(Continued)

OTHER PUBLICATIONS

Bhattacharyya, "Reactively compatibilised polyamide6/ethylene-co-vinyl acetate blends: Mechanical properties and morphology", Polymer, Feb. 14, 2005, v 46 n 5, p. 1661-1674.

(Continued)

*Primary Examiner*—Robert D. Harlan
(74) *Attorney, Agent, or Firm*—Brooks, Cameron & Huebsch, PLLC

(57) ABSTRACT

Reinforced copolymers formed from a functionalized copolymer that undergoes a reactive extrusion process with an inorganic component to form the reinforced copolymer. The functionalized copolymer in the form of a block and/or graft copolymer includes hard segments and soft segments, where the soft segments are covalently bonded with a coupling agent either before or after copolymerization with the hard segments. The reinforced copolymer of the present disclosure can be suitable for use as a biomaterial and/or in medical devices.

14 Claims, No Drawings

U.S. PATENT DOCUMENTS

| | | |
|---|---|---|
| 2005/0055077 A1 | 3/2005 | Marco et al. |
| 2005/0070913 A1 | 3/2005 | Milbocker et al. |
| 2005/0090612 A1 | 4/2005 | Soane et al. |
| 2005/0142163 A1 | 6/2005 | Hunter et al. |
| 2005/0147562 A1 | 7/2005 | Hunter et al. |
| 2005/0147599 A1 | 7/2005 | Hunter et al. |
| 2005/0147643 A1 | 7/2005 | Hunter et al. |
| 2005/0148512 A1 | 7/2005 | Hunter et al. |
| 2005/0149046 A1 | 7/2005 | Friedman et al. |
| 2005/0158274 A1 | 7/2005 | Hunter et al. |
| 2005/0169958 A1 | 8/2005 | Hunter et al. |
| 2005/0169959 A1 | 8/2005 | Hunter et al. |
| 2005/0175657 A1 | 8/2005 | Hunter et al. |
| 2005/0175665 A1 | 8/2005 | Hunter et al. |
| 2005/0175703 A1 | 8/2005 | Hunter et al. |
| 2005/0178395 A1 | 8/2005 | Hunter et al. |
| 2005/0178396 A1 | 8/2005 | Hunter et al. |
| 2005/0182463 A1 | 8/2005 | Hunter et al. |
| 2005/0183731 A1 | 8/2005 | Hunter et al. |
| 2005/0186244 A1 | 8/2005 | Hunter et al. |
| 2005/0186247 A1 | 8/2005 | Hunter et al. |
| 2005/0187140 A1 | 8/2005 | Hunter et al. |
| 2005/0191248 A1 | 9/2005 | Hunter et al. |
| 2005/0196421 A1 | 9/2005 | Hunter et al. |
| 2005/0208095 A1 | 9/2005 | Hunter et al. |
| 2005/0209674 A1 | 9/2005 | Kutscher et al. |
| 2005/0232964 A1 | 10/2005 | Fennimore, Jr. |
| 2005/0272806 A1 | 12/2005 | Falotico et al. |
| 2005/0283255 A1 | 12/2005 | Geremakis et al. |
| 2006/0036052 A1 | 2/2006 | Kindt-Larsen et al. |

FOREIGN PATENT DOCUMENTS

| | | |
|---|---|---|
| EP | 0 646 143 | 10/2000 |
| EP | 0 726 922 | 6/2002 |
| EP | 0 887 200 | 9/2004 |
| EP | 0 909 800 | 9/2004 |
| EP | 1 216 146 | 10/2005 |
| EP | 1 171 496 | 12/2005 |
| WO | WO 95/12630 | 5/1995 |
| WO | WO 97/20521 | 6/1997 |
| WO | WO 98/42793 | 10/1998 |
| WO | WO 99/38817 | 8/1999 |
| WO | WO 00/56795 | 9/2000 |
| WO | WO 00/64969 | 11/2000 |
| WO | WO 00/65352 | 11/2000 |
| WO | WO 02/17883 | 3/2002 |
| WO | WO 02/41417 | 5/2002 |
| WO | WO 02/43937 | 6/2002 |
| WO | WO 03/023401 | 3/2003 |
| WO | WO 2004/005533 | 1/2004 |
| WO | WO 2004/007608 | 1/2004 |
| WO | WO 2004/013058 | 2/2004 |
| WO | WO 2004/026936 | 4/2004 |
| WO | WO 2004/065295 | 8/2004 |
| WO | WO 2005/026229 | 3/2005 |
| WO | WO 2005/037911 | 4/2005 |
| WO | WO 2005/118018 | 12/2005 |
| WO | WO 2005/119828 | 12/2005 |
| WO | WO 2005/123023 | 12/2005 |

OTHER PUBLICATIONS

Di Lorenzo, "Calorimetry of nanophase-separated poly(oligoamide-altoligoether)s", Journal of Polymer Science Part B-Polymer Physics, Jul. 15, 2001, v 39 n 14. p. 1594-1604.

Wu, "Modification of polyethylene-octene elastomer by silica through a sol-gel process", Journal of Applied Polymer Science, Apr. 25, 2003, v 88 n 4, p. 966-972.

Tseng, "Poly(oxypropylene)-amide grafted polypropylene as novel compatibilizer for PP and PA6 blends", Polymer, Jan. 2001, v 42 n 2, p. 713-725.

Pnadya, "Synthesis and characterization of nylon 6 triblock copolymer using new hybrid soft segment", Eur. Poly. J.,1997, vol. 33 No. 6, pp. 789-794.

McClusky, "Modification of polyurethane elastomer properties by control of hard domain formation", Polymer Preprints,1998, vol. 39 No. 2, pp. 661-662.

* cited by examiner

FUNCTIONALIZED BLOCK COPOLYMERS

BACKGROUND OF THE DISCLOSURE

Dilation catheters are used for opening blood vessels or other passageways in the body that may be blocked by obstructions or stenosis. Dilatation catheters are generally formed from thin, flexible tubing having an inflatable balloon at or near a distal tip of the catheter that can be inflated with fluid pressure communicated to the balloon through a lumen of the catheter. In a typical angioplasty procedure, the balloon dilatation catheter is passed through the vasculature to the location of a stenosis in an artery, and the balloon is inflated to a predetermined size and shape to open the blocked artery.

It is desirable for balloons of balloon dilatation catheters to be capable of inflating to a diameter of typically many times their uninflated diameter in order to be able to open an obstructed vessel. Other desirable properties of balloons for such balloon dilatation catheters include strength, softness, flexibility and a thin, low profile which are important for achieving the performance characteristics of folding in an uninflated state, tracking, crossing and recrossing the area of the obstruction or stenosis in a vessel in an uninflated state. In addition, properties of burst strength, compliance, and fatigue have been increasingly important in the continuing effort to create thinner, lower profile balloons for dilatation catheters with an ability to track, cross and recross increasingly narrow passages in obstructed vessels.

Polymeric materials that have been used for making medical devices, catheters, dilatation catheters, and balloons for dilatation catheters include polyethylene, polyolefins, polyvinyl chloride, polyester, polyamide, polyethylene terephthalate (PET), polyamides, polyurethane, and the like. Balloons made of soft polyolefin or ethylene copolymers materials are typically foldable, and track and cross well, so that they can often be used more than once, and can be used to cross multiple lesions. However, such balloons also commonly have high balloon compliance and low burst strengths. Balloons made from polyethylene terephthalate (PET) are commonly stronger, with a higher rated burst pressure. However, dilatation catheter balloons made of PET are generally stiff, not readily foldable and refoldable, and are susceptible to acquiring defects from mechanical handling.

It would be desirable to provide a polymeric blend for balloons of balloon dilatation catheters with a combination of the best features of the softer balloon materials and the stronger balloon materials, including good flexibility, folding, track, cross and recross, with a thin, low profile, high resistance to fatigue, low compliance, and high burst strength.

DETAILED DESCRIPTION OF DISCLOSURE

The present disclosure relates to catheters and balloons for medical catheters formed from a reinforced copolymer having certain characteristics generally desirable in medical devices. The reinforced copolymer described herein is particularly suitable for use in forming medical products such as catheters, dilatation catheters, and balloons of dilatation catheters.

The reinforced copolymer of the present disclosure is formed from a functionalized copolymer that undergoes a reactive extrusion process with an inorganic component to form the reinforced copolymer. The functionalized copolymer in the form of a block and/or graft copolymer includes hard segments and soft segments, where the soft segments are covalently bonded with a coupling agent either before or after copolymerization with the hard segments. In one embodiment, the coupling agent can covalently bond with the inorganic component during the reactive extrusion process to form the reinforced copolymer. Alternatively, the functionalized copolymer can act as a compatibilizer to facilitate blending the functionalized copolymer with other polymers.

The reinforced copolymer of the present disclosure can be suitable for use as a biomaterial and/or in medical devices. The reinforced copolymer display excellent performance in many characteristics important for medical device use, including compressive strength, diametral tensile strength, flexural strength, fracture toughness, puncture resistance, hardness, changes in hydrophobicity, adhesion, non-adhesion, friction, patency or biointegration of the device with one or more tissue surfaces of a body of a patient depending on the particular application of the device, resistance to wear (e.g., characterized by compressive strength and diametral tensile strength), durability, thermal expansion, visual opacity, x-ray opacity, impact strength, chemical durability, electrical conductivity, biocompatibility, modulus, shelf life, patient comfort, ease-of-use, and structural integrity relative to a polymer without the inorganic component that is used in forming the reinforced copolymer.

In addition, the reinforced copolymer of the present disclosure can be further characterized in that it can be substantially insoluble in body fluids and tissues and that is designed and constructed to be placed in or onto the body or to contact fluid or tissue of the body. Ideally, the reinforced copolymer will be biostable, biocompatible, and will not induce reactions in the body such as blood clotting, tissue death, tumor formation, allergic reaction, foreign body reaction (rejection) or inflammatory reaction; will have the physical properties such as strength, elasticity, permeability and flexibility required to function for the intended purpose; can be purified, fabricated and sterilized; and will substantially maintain its physical properties and function during the time that it remains implanted in or in contact with the body. A "biostable" material is one that is not broken down by the body, whereas a "biocompatible" material is one that is not rejected by the body.

As used herein, a "medical device" can be defined as a device that has surfaces that contact blood or other body fluids and/or tissues in the course of their operation. This can include, for example, extracorporeal devices for use in surgery such as blood oxygenators, blood pumps, blood sensors, tubing used to carry blood and the like which contact blood which is then returned to the patient. This can also include devices such as vascular grafts, stents, electrical stimulation leads, valves for use in the cardiac system (e.g., heart valves), orthopedic devices, intracorporeal or extracorporeal devices (e.g., catheters), catheter shaft components, filters, guide wires, shunts, clamps, sensors, membranes, balloons (e.g., dilatation balloons), anastomotic devices, aneurysm repair devices, embolic devices, implantable devices (e.g., orthopedic implants), replacement devices for nucleus pulposus, cochlear or middle ear implants, intraocular lenses, coatings for such devices, and the like that comprise reinforced copolymers.

Reinforced copolymers of the present disclosure can be used in medical devices as well as nonmedical devices. As discussed, they can be used in medical devices and are suitable as biomaterials. Examples of medical devices are listed herein. Examples of nonmedical devices include foams, insulation, clothing, footwear, paints, coatings, adhesives, and building construction materials, besides others.

As used herein, the terms "a," "an," "the," "one or more," and "at least one" are used interchangeably and include plural referents unless the context clearly dictates otherwise. Unless defined otherwise, all scientific and technical terms are understood to have the same meaning as commonly used in the art to which they pertain. For the purpose of the present disclosure, additional specific terms are defined throughout.

As used herein, a "reinforced copolymer" refers to a functionalized copolymer that includes, at least in part, an inorganic component covalently bonded thereto and any desired filler and/or adjuvants. In one embodiment, the copolymer used to form the functionalized copolymer is a thermoplastic having a block copolymer and/or a graft copolymer configuration. The copolymer can include one or more each of an A-Block and a B-Block for either of the block copolymer and/or graft copolymer configurations, as discussed herein.

For the present disclosure, the A-Block is a soft-segment polymer and the B-Block is a hard-segment polymer as compared to the A-Block. Each "block" or segment of the copolymer may be a homopolymer, or a random or block copolymer itself. As used herein, a "hard-segment" polymer is one that includes a majority of either crystalline domains (i.e., has ordered domains) at use temperature or amorphous domains with a glass transition temperature above use temperature (i.e., glassy), and a "soft-segment" polymer is one that includes a majority of amorphous domains with a glass transition temperature below use temperature (i.e., rubbery). Typically, hard segments add considerable strength and higher modulus to the copolymer. Similarly, soft segment adds flexibility and lower modulus, but may add strength particularly if it undergoes strain crystallization, for example. The copolymers can vary from hard and rigid to soft and flexible. In one example, the copolymers can be elastomers. An "elastomer" is a polymer that is capable of being stretched to approximately twice its original length and retracting to approximately its original length upon release.

Soft-segment polymers for the A-Block can be selected from the group consisting of polyoxyalkene glycols such as polyoxyethylene (PEO) and/or polytetramethylene ether glycol (PTMEG, Terathane®), polyethylene octene elastomer (POE), poly(oxypropylene) (POP), and polyethylene butene elastomer or other suitable aliphatic soft polymer moieties, optionally polymerized with other monomers. Combinations of the soft-segment polymers are also possible. Other soft-segment polymers are also possible.

Examples of hard-segment polymers for the B-Block can be selected from polyamide, polyimide, polyethylene terephthalate (PET), polyesters, polypropylene, or other suitable aliphatic hard polymer long-chain organic units that includes urethane groups, urea groups, ether groups, ester groups, or combinations thereof (e.g., polyurethanes, polyureas, or polyurethane-ureas) in the B-Block. Other hard-segment polymers are also possible.

As used herein, "long-chain" refers to an organic connecting unit (i.e., connecting the A-Blocks) containing 20 atoms or more (preferably, 20 carbon atoms or more). As used herein, the term "organic unit" refers to a hydrocarbyl group (aliphatic and/or aromatic) optionally including other atoms (e.g., heteroatoms) or groups (e.g., functional groups) replacing the carbon and/or hydrogen atoms. The term "aliphatic group" means a saturated or unsaturated linear (i.e., straight chain), cyclic, or branched hydrocarbon group. This term is used to encompass alkyl (e.g., $-CH_3$) (or alkylene if within a chain such as $-CH_2-$), alkenyl (or alkenylene if within a chain), and alkynyl (or alkynylene if within a chain) groups, for example. The term "alkyl group" means a saturated linear or branched hydrocarbon group including, for example, methyl, ethyl, isopropyl, t-butyl, heptyl, dodecyl, octadecyl, amyl, 2-ethylhexyl, and the like. The term "alkenyl group" means an unsaturated, linear or branched hydrocarbon group with one or more carbon-carbon double bonds, such as a vinyl group. The term "alkynyl group" means an unsaturated, linear or branched hydrocarbon group with one or more carbon-carbon triple bonds. The term "aromatic group" or "aryl group" means a mono- or polynuclear aromatic hydrocarbon group. These hydrocarbon groups may be substituted with heteroatoms, which can be in the form of functional groups. The term "heteroatom" means an element other than carbon (e.g., nitrogen, oxygen, sulfur, chlorine, etc.).

Polymers used to form the A-Blocks and B-Blocks can be prepared using a variety of techniques from polymerizable compounds (e.g., monomers, oligomers, or polymers). Such compounds include diols, diamines, diacids, diisocyantes, or combinations thereof, for example. The method to prepare the block and/or graft copolymer can be by any of the methods generally known for block and/or graft polymerizations. Embodiments of the copolymer can include a di-block, tri-block or multi-block copolymer. In the case of the tri-block or multi-block copolymer, different configurations of block order are included in the present disclosure. In addition, the molecular weight (i.e., average molecular weights) of the various blocks can be modified and adjusted to help determine processing characteristics and end-use performance properties of the copolymer used in the present disclosure. The molecular weights of the block copolymers can be controlled by well-known synthetic techniques, where the molecular weights of the copolymer used for the reinforced copolymer may vary depending on the desired properties and use.

Typically, the A-B block copolymers are prepared from precursor polymers (i.e., prepolymers), although other methods can be used to build polymers with the same block architecture. In one embodiment, the B-Block is formed from an acidic functional precopolymer (e.g., a monofunctional and/or difunctional carboxylic acid polyamide (HOOC—PA-COOH) or polyimide (HOOC—PI—COOH)) and the A-Block is formed from a hydroxyl functional precopolymer (e.g., a monofunctional and/or difunctional polyoxyethylene (HO—PEO—OH)), where the copolymerization reaction is carried out under vacuum and with tetraalkylorthotitante as a catalyst, as discussed in U.S. Pat. Nos. 4,230,838, 4,331,786 and 4,332,920 all to Foy et al., which are incorporated herein by reference in their entirety.

Alternatively, the B-Block is formed from an acidic functional precopolymer (e.g., a monofunctional and/or difunctional carboxylic acid polyamide (HOOC—PA-COOH) or polyimide (HOOC—PI—COOH)) and the A-Block can be formed from an amine functional precopolymer (e.g., a monofunctional and/or difunctional polymethylenediamine ($H_2N-(CH_2)_n-NH_2$)), where n is in the polymeric range. In an additional embodiment, the B-Block is formed from an isocyanate functional precopolymer (e.g., a monofunctional and/or difunctional isocyanate polyamide (OCN—PA-NCO) or polyimide (OCN—PI—NCO)) and the A-Block is formed from a hydroxyl functional precopolymer (e.g., a monofunctional and/or difunctional polyoxyethylene (HO—PEO—OH)).

Although certain polymers are described herein, the polymers used to form the B-Blocks of the A-B Block copolymers for the present disclosure can be from a wide variety of polymers that include polyamide groups, polyimide groups, or combinations thereof. Such polymers are prepared from acid-containing compounds, such as polycarboxylic acids (e.g., dicarboxylics), and compounds having at least two hydrogen atoms reactive with the acid groups, such as polyamines (e.g., diamines).

Each of the individual A-Blocks and B-Blocks, as well as the resultant copolymer, may be linear or branched, although not so significantly branched that the resultant polymer is not thermoplastic. Because the B-Block can be branched, it is envisioned that the A-B block copolymer could be a star block copolymer, for example.

The copolymer according to the present disclosure can be obtainable by reactive processing of a mixture comprising the A-Block polymer and the B-Block polymer, as discussed herein, in a melt-mixing process, i.e., reactive processing the polymers together in an internal mixer, a single screw extruder, a co- or counter rotating twin-screw extruder, an open mill or any other type of equipment suitable and known in the art. Preferred conditions for forming the A-B Block copolymer include the use of an inert atmosphere (e.g., nitrogen or argon), temperatures of about 20° C. to about 150° C., and reaction times of about 1 hour to about 3 days. The A-Block and B-Block precursors are typically combined under such conditions to form the A-B Block copolymers of the present disclosure. Other reaction schemes are also possible.

In an additional embodiment, additional block copolymers suitable for use in the present disclosure include, but are not limited to, polyamide/polyether block copolymers such as those sold under the trade name "PEBAX" by Elf Atochem.

The present disclosure further provides that the soft segment polymers forming the A-Block can be functionalized with a coupling agent. In one embodiment, the A-Block polymers can be functionalized with the coupling agent in a number of ways. For example, the A-Block polymers can be functionalized by reacting the A-Block polymers with a coupling agent such as a cyclic anhydride, or other suitable like materials. In addition, the coupling agent is not covalently coupled to the B-Block polymer hard segments. The resulting functionalized copolymer (i.e., the copolymer of the B-Block and A-Block polymer having the covalently bonded coupling agent) can then react with the inorganic component during a reactive extrusion process to form the reinforced copolymer of the present disclosure.

Alternatively, the functionalized copolymer of the present disclosure can be used as a compatibilizer for blending and/or reacting with one or more additional polymers. When used as a compatibilizer the functionalized copolymer can be used to blend, for example, polar with non-polar polymers selected from polar/non-polar thermoplastic elastomers, non-polar polyolefins/polar thermoplastic elastomers and non-polar thermoplastic elastomers/engineering resins.

According to the present disclosure, the A-Block polymers can be functionalized with the coupling agent prior to being copolymerized with the B-Block polymers. Alternatively, functionalization with the coupling agent can take place after copolymerization of the A-Block and B-Blocks. The functionalized copolymer of the present disclosure can then be modified with the inorganic component, as will be discussed herein, by reacting the functionalized copolymer with the inorganic component in a reactive extrusion process to form the reinforced copolymer of the present disclosure. The reactive extrusion process can be carried out in conventional polymer processing equipment such as a single screw extruder, a twin screw extruder, a two roll mill, or a Henschel type of mixer, and the like.

Typically, the coupling agent(s) can be added to the A-Block polymer after the polymers (e.g., the A-Block alone, or the A-B Block copolymer) have been molten and blended. The reaction temperature depends on the melting-point of the polymer and is typically 150° C. to 250° C. Free radical source suitable for use in the process of the present disclosure are those materials typically used for the A-Block polymers provided herein that exhibit free radical generation in the melt processing range typically used for such polymers. Specific examples include acyl peroxides, such as benzoyl peroxide; dibenzoyl peroxide, dialkyl, diaryl, or aralkyl peroxide, such as di-t-butyl peroxide; dicumyl peroxide; cumyl butyl peroxide; 1,1-di-t-butyl peroxy-3,5,5-trimethylcyclohexane; 2,5-dimethyl-2,5-di(t-butylperoxy) hexane; 2,5-dimethyl-2,5-bis-(t-butylperoxy) hexyne-3 and bis(a-t-butyl peroxyisopropylbenzene); peroxyesters such as t-butyl peroxypivalate; t-butyl peroctoate; t-butyl perbenzoate; 2,5-dimethylhexyl-2,5-di(perbenzoate) t-butyl di(perphthalate); dialkyl peroxymonocarbonates and peroxydicarbonates; hydroperoxides, such as t-butyl hydroperoxide, p-methane hydroperoxide, pinane hydroperoxide and cumene hydroperoxide and ketone peroxides, such as cyclohexanone peroxide, methyl ethyl ketone peroxide, and the like.

The free radical source is generally used in the process according to the present disclosure in a sufficient quantity to make it possible to effect the coupling of the coupling agent. Furthermore, it is desirable that the quantity should not exceed the minimum quantity needed because any excess of radical-generator may results in a degradation of the copolymer and/or may create undesirable cross-linking of the copolymer.

Examples of cyclic anhydrides useful for making the functionalized copolymer for the reinforced copolymer according to the present disclosure are selected from the group consisting of maleic anhydride, succinic anhydride, hexahydrophthalic anhydride, tetrahydrophthalic anhydride, dodecylsuccinic anhydride, phthalic anhydride, nadic anhydride, pyromellitic anhydride, and mixtures thereof. A cyclic anhydride, which is particularly useful in certain embodiments of the disclosure, is maleic anhydride. The molecular weights of the cyclic anhydrides useful for making the reinforced copolymer may vary depending on the desired properties and use.

As used herein, the inorganic component servers as a reinforcement in the reinforced copolymer. A reinforcement may be defined simply as the material that is added to the functionalized copolymer of the present disclosure to improve the strength of the copolymer. As is appreciated, the relative amounts of the various ingredients will depend in part upon the particular end use and on the particular reinforced copolymer that is selected for the particular end use.

Most of the reinforcing materials are inorganic products of high molecular weight. Various examples include glass fibers, boron fibers, carbon and graphite fibers, whiskers, quartz and silica fibers, ceramic fibers, and metal fibers. It is also possible to use organic reinforcements with the functionalized copolymer, such as natural organic fibers, and synthetic organic fibers.

A useful reinforcement for the reinforced copolymer of the present disclosure is inorganic components formed from sol-gel preparations of at least one silicon alkoxide. The resulting sol-gel preparations can be bonded to the functionalized copolymer through reacting with the coupling agent in the reactive extrusion process. In one embodiment, the sol-gel preparations are formed from at least one silicon alkoxide of the formula (Formula I):

wherein R is an organic group. Examples of such organic groups include a straight chain or branched alkyl group, a straight chain or branched alkylene group, where R optionally includes heteroatoms that may be in the chain of the organic group or pendant therefrom as in a functional group.

As used herein, the term "organic group" is used for the purpose of this disclosure to mean a hydrocarbon group that is classified as an aliphatic group. In the context of the present disclosure, suitable organic groups for the silicon alkoxide of this disclosure are those that do not interfere with the formation of sol-gel preparations.

In one embodiment, each R is independently a straight chain or branched alkyl group optionally including heteroatoms, such as nitrogen, oxygen, phosphorus, sulfur, and halogen. The heteroatoms can be in the backbone of R or pendant therefrom, and they can form functional groups such as heteroatom-containing groups (e.g., functional groups) include, for example, an alcohol, carbonyl, ether, acetoxy, ester, aldehyde, acrylate, amine, amide, imine, imide, and nitrile, whether they be protected or unprotected. In one embodiment, R does not include heteroatoms. In an additional embodiment, each R is independently a straight chain or branched alkyl group includes 18 carbon atoms or less. In a further embodiment, each R is independently a straight chain or branched (C2-C8) alkyl group. In other embodiments, each R is independently a straight chain or branched (C2-C4) alkyl group (e.g., ethyl, n-propyl, isopropyl, or butyl). In one example, R is a C2 alkyl group.

As will be appreciated, for Formula I, R can vary within any one of the sol-gel preparations. For example, in addition to each R being the same or different within each $Si(OR)_4$, the OR groups can be the same or different in any one sol-gel preparation.

Although certain sol-gel preparations are described herein, the sol-gel preparations used in the present disclosure can be formed in a cross-linking process from a wide variety of silicon alkoxides of Formula I. For example, a method of preparing the sol-gel preparations involves the combining of at least one silicon alkoxide of the Formula I under sol-gel reaction conditions to form a reaction mixture allowing the sol-gel preparations to form in the reaction mixture.

The Sol-gel processes is generally described, for example, in "Sol-Gel Science: The Physics and Chemistry of Sol-Gel Processing" (Brinker et al., Academic Press, 1990). As used herein, "sol-gel" refers to any method of synthesizing the sol-gel preparations that comprises a step wherein at least one of the precursors is an aqueous or organic dispersion, sol, or solution.

Three reactions are generally used to describe the sol-gel process: hydrolysis, alcohol condensation, and water condensation. The characteristics and properties of the sol-gel preparations formed through the sol-gel process with compounds of Formula I can be related to a number of factors that affect the rate of hydrolysis and condensation reactions, such as, pH, temperature and time of reaction, reagent concentrations, catalyst nature and concentration, aging temperature and time, and drying. Controlling these factors allow for the structure and properties of the sol-gel preparations to be varied as desired.

A method for preparing the sol-gel preparations for the present disclosure through a sol-gel process involves the combining of (1) the mixture of the compound(s) of Formula I and (2) an aqueous or organic dispersion or sol of reagents that include at least one alcohol and a catalyst provided under conditions for the sol-gel reaction to take place. Examples of silicon alkoxides of Formula I include normal and branched butoxides, propoxides, ethoxides, and methoxides of silicon (Si) and mixtures thereof. Specific examples of suitable silicon alkoxide of Formula I include tetraethoxysilane (TEOS), and the like.

Examples of suitable catalysts include mineral acids such as hydrochloric acid (HCl), ammonia, acetic acid, potassium hydroxide (KOH), titanium alkoxides, vandium alkoxides, amines, KF, and HF. Additionally, it has been observed that the rate and extent of the hydrolysis reaction is most influenced by the strength and concentration of the acid- or base catalyst. In one embodiment, the concentration of the acid- or base-catalyst can be from 0.01 M to 7M. In addition, the nature of the sol-gel reaction can be influenced by the selection of an acid or base catalyst, where under acid-catalyzed conditions the sol-gel reaction yields primarily linear or randomly branched polymers which entangle and form additional branches resulting in gelation. On the other hand, the sol-gel reaction yields derived under base-catalyzed conditions can yield more highly branched clusters which behave more like discrete clusters.

Examples of suitable alcohols include anhydrous alcohol such as methanol, ethanol, propanol, butanol, pentanol, and mixtures thereof. Suitable alcohols have a water content of less than about 1% by weight, especially less than about 0.5% by weight or less than about 0.1% by weight. Other organic solvent (or mixtures of solvents) may also be used that are miscible with the other components.

Examples of suitable alcohols include anhydrous alcohol such as methanol, ethanol, propanol, butanol, pentanol, and mixtures thereof. Suitable alcohols have a water content of less than about 1% by weight, especially less than about 0.5% by weight or less than about 0.1% by weight. Other organic solvent (or mixtures of solvents) can also be used that are miscible with the other components.

According to the present disclosure, the sol-gel reaction can take place with the reagents in either a liquid phase and/or a gas phase. Typical reaction conditions for the sol-gel reaction can occur in a temperature range of 20° C. to 100° C. Other temperature ranges are also possible.

The method of forming the medical device and/or medical device component can then include (1) preparing the reinforced copolymer in the reactive extrusion process with the functionalized copolymer and the sol-gel preparation, and (2) forming the reinforced copolymer prepared from the extrusion into the predetermined shape of the medical device component. As discussed herein, preparing the reinforced copolymer in the reactive extrusion process includes combining the sol-gel preparations with the functionalized copolymer during the melt process to form the reinforced copolymer. The reinforced copolymer may contain a sufficient amount by weight percent of the sol-gel preparations that do not interfere with either the sol-gel preparations and/or the processing of the reinforced polymer.

The reinforced copolymer of the present disclosure can be utilized in several different ways: 1) on its own, (2) combined with one or more additional thermoplastics (co-block polymers—PEBAX®, polyamides), PET, etc. to alter the final properties of the reinforced copolymer. Furthermore, other components known in the art may be added to the graft polymers of this disclosure to further enhance the properties of the final material. All of these additives are generally used in relatively small amounts as compared to the weight percent of the final composition. Applications for the reactive extruded reinforced copolymer produced according to the present disclosure include films, injection molded articles (e.g., dilatation balloons), extruded profiles, fiber additives, and barrier containers.

The present disclosure provides for a reactive extrusion process of the functionalized copolymer and inorganic components to form the reinforced copolymer. As used herein, a "reactive extrusion process" is the use of chemical reactions during a polymer extrusion process to form desired products. Specifically, the present disclosure provides for coupling of a cyclic anhydride onto the A-Block polymer of the A-B Block copolymer followed by covalently coupling the inorganic components through the coupling agent during the reactive extrusion process.

Free radical initiators, crosslinking agents, and other reactive additives can be injected into the reactive extrusion process to cause and/or promote the coupling reactions discussed herein. In addition, while the reactive extrusion process may result in production of a homogeneous product, a somewhat heterogeneous product is within the scope of this disclosure. Examples of such processes and/or techniques include, but are not limited to, mixing process that include screw extrusion (single or twin barrel), among others.

The melt extruder used in the reactive extrusion process of the present disclosure is designed to conduct several operations during the preparation of the melt reactive extrusion. The reinforced copolymers of the present disclosure are produced in the reactive extrusion process. In one embodiment, it is desired according to the present disclosure to blend or mix the A-B Block copolymer, the coupling agent (e.g., the cyclic anhydride), a free radical source, and the sol-gel preparations in an extruder, such as a single-screw or twin-screw extruder under appropriate temperature and shear/pressure conditions to ensure mixing.

A particularly desirable reaction device is an extruder having one or more ports. For example, the reaction device is a co-rotating, twin-screw extruder, that allows multiple feeding and venting ports and provides high intensity distributive and dispersive mixing that is essential to produce functionalized copolymers of uniform composition and homogeneous distribution of the sol-gel preparations in the functionalized copolymer. The reactions are desirably conducted in the polymer melt phase; i.e., in the absence of bulk solvent. This is an effective process since the solvent removal step is not needed in the process.

In one embodiment, the A-B Block copolymer is fed into and melted in the melt extruder. After melting the A-B Block copolymer, the coupling agent (e.g., the cyclic anhydride) is fed into and melt blended in the melt extruder and, further down the extruder barrel, the free radical source, such as a peroxide, is fed to the extruder to yield improved coupling efficiency of the coupling agent to form the functionalized copolymer. After a length of extrusion sufficient to accomplish coupling of the coupling agent, i.e., sufficient time, the sol-gel preparations are fed to the molten, functionalized copolymer stream either as pellets or powder through an open throat to the extruder or as a molten stream fed through a side stream extruder. After melt consolidation of the functionalized copolymer and the sol-gel preparations, a vacuum port can optionally be used to remove ungrafted or unreacted coupling agent (e.g., cyclic anhydride).

By coupling the coupling agent onto the A-B Block copolymer, the resulting functionalized copolymer is more compatible with and reactive to the sol-gel preparations. The compatibility of the functionalized copolymer of the present disclosure with the sol-gel preparations can be controlled by the selection of the coupling agent, the level of coupling and the blending process conditions. Tailoring the compatibility of the functionalized copolymer with the sol-gel preparations leads to better processability and improved physical properties of the resulting reinforced copolymer.

The resulting reinforced copolymer can then be processed in a number of ways into a predetermined shape. Processes useful with the reinforced copolymer include, but are not limited to, injection molding, compression molding, over molding, dipping, extrusion, roto-molding, slush molding, fiber spinning, blow molding, polymer modification, cast film making, blown film making and foaming. In addition, the resulting reinforced copolymer can also be coated onto or coextruded with a substrate in forming the medical device component.

Included with the predetermined shapes are both balloon dilatation catheters and the dilatation balloons, as are known. The reinforced copolymer of the present invention can be used to form dilatation balloons by known techniques such as free-blowing or through molding techniques. As is known, the molding techniques can include positioning tubing formed from the reinforced copolymer of the present disclosure in a blow molding apparatus. One end of the tubing can then be connected to a source of pressurized gas, while the other end of the tubing extending beyond the mold can be clamped, or otherwise sealed, during pressurization of the tubing. The tubing can also be affixed to a tensioning device. The tubing within the mold is then heated to a desired temperature below the crystalline melting point of the tubing, such as until the material deforms, for example. During heating, or optionally after heating, pressurized gas is applied to the tubing, and optionally tension is also applied to the tubing, until the balloon is formed, filling the desired interior shape of the mold. The balloon and tubing are then cooled to room temperature. The balloon is then removed from the mold, and can be further processed to construct a dilatation catheter.

The reinforced copolymers of the present disclosure can be compounded with other components not adversely affecting the reinforced copolymer properties. Exemplary materials that could be used as additional components would include, without limitation, pigments, antioxidants, stabilizers, surfactants, processing lubricants, imaging enhancers, fillers, and the like.

The disclosure has been described with reference to various embodiments. It is understood, however, that there are many extensions, variations, and modification on the basic theme of the present disclosure beyond those discussed in the detailed description that are within the spirit and scope of the present disclosure.

The complete disclosures of the patents, patent documents, and publications cited herein are incorporated by reference in their entirety as if each were individually incorporated. Various modifications and alterations to this disclosure will become apparent to those skilled in the art without departing from the scope and spirit of this disclosure. It should be understood that this disclosure is not intended to be unduly limited by the illustrative embodiments set forth herein and that such embodiments are presented by way of example only with the scope of the disclosure intended to be limited only by the claims set forth herein as follows.

What is claimed is:

1. A reinforced copolymer comprising:
    a copolymer having soft segments and hard segments;
    a coupling agent covalently coupled to the soft segments, where the coupling agent is not covalently coupled to the hard segments;
    an inorganic component coupled to the soft segments of the copolymer to form the reinforced copolymer.

2. The reinforced copolymer of claim 1, where the reinforced copolymer is formed from a functionalized copolymer that undergoes a reactive extrusion process with the inorganic component to form the reinforced copolymer.

3. The reinforced copolymer of claim 1, where the copolymer is at least one of a block copolymer and a graft copolymer having A-Blocks for the soft segments and B-Blocks for the hard segments.

4. The reinforced copolymer of claim 3, where the soft-segment polymers for the A-Block are selected from the group consisting of polyoxyalkene glycols, polyethylene octene elastomer (POE), poly(oxypropylene) (POP), polyethylene butene elastomer, and combinations thereof.

5. The reinforced copolymer of claim 3, where the hard-segment polymers for the B-Block are selected from the group consisting polyamide, polyimide, polyethylene terephthalate (PET), polyesters, polypropylene, polyurethanes, polyureas, polyurethane-areas, and combinations thereof.

6. The reinforced copolymer of claim 3, where the copolymers is prepared from precursor polymers in which the B-Block is formed from at least one of an acidic functional precopolymer and a polyimide functional precopolymer, and the A-Block is formed from a hydroxyl functional precopolymer.

7. The reinforced copolymer of claim 3, where the copolymers is prepared from precursor polymers in which the B-Block is formed from at least one of an acidic functional precopolymer and a polyimide functional precopolymer and the A-Block is formed from an amine functional precopolymer.

8. The reinforced copolymer of claim 3, where the copolymers is prepared from precursor polymers in which the B-Block is formed from at least one of an isocyanate functional precopolymer and polyimide functional precopolymer and the A-Block is formed from a hydroxyl functional precopolymer.

9. The reinforced copolymer of claim 1, where the copolymer is a polyamide/polyether block copolymer.

10. The reinforced copolymer of claim 1, where the coupling agent is a cyclic anhydride selected from the group consisting of maleic anhydride, succinic anhydride, hexahydrophthalic anhydride, tetrahydrophthalic anhydride, dodecylsuccinic anhydride, phthalic anhydride, nadic anhydride, pyromellitic anhydride, and mixtures thereof.

11. The reinforced copolymer of claim 1, where the inorganic component is a reinforcing material selected from the group consisting of glass fibers, boron fibers, carbon and graphite fibers, whiskers, quartz and silica fibers, ceramic fibers, metal fibers, and sol-gel preparations.

12. The reinforcement copolymer of claim 1, where the inorganic component is a sol-gel preparation formed from at least one metal alkoxide.

13. The reinforcement copolymer of claim 1, where the reinforcement copolymer is used to form a dilatation balloon for a dilatation catheter.

14. A medical device prepared from the reinforced copolymer of claim 1.

* * * * *